United States Patent [19]

Zaltsman

[11] 4,136,775
[45] Jan. 30, 1979

[54] MIXING CAPSULE

[75] Inventor: Saul Zaltsman, Savyon, Israel

[73] Assignee: Silmet Ltd., Givatayim, Israel

[21] Appl. No.: 825,395

[22] Filed: Aug. 17, 1977

[30] Foreign Application Priority Data

Aug. 10, 1977 [IL] Israel .................................. 52695

[51] Int. Cl.² .............................................. B65D 81/32
[52] U.S. Cl. .................................. 206/219; 32/40 A; 366/602
[58] Field of Search ................. 366/602, 241, 255; 32/40 A; 206/219, 220, 222

[56] References Cited

U.S. PATENT DOCUMENTS

| | | | |
|---|---|---|---|
| 2,487,236 | 11/1949 | Greenberg | 366/602 X |
| 3,809,225 | 5/1974 | Coche | 206/220 |
| 3,831,742 | 8/1974 | Gardella | 206/219 |
| 3,860,114 | 1/1975 | Merckardt | 206/219 |
| 3,963,120 | 6/1976 | Perfect | 206/219 |

Primary Examiner—Edward J. McCarthy
Attorney, Agent, or Firm—Benjamin J. Barish

[57] ABSTRACT

A mixing capsule for mixing a first material with a second material (e.g. to prepare a dental silver amalgam) comprises a pair of tubular housing sections removably attached to each other and defining between them a first chamber for receiving the first material to be mixed. The second housing section includes a partition integrally joined to its inner surface by a thin connecting web, and a tubular neck above the partition. A plunger is disposed in the neck of the second housing section, the lower face of the plunger defining with the partition a second chamber for receiving the second material to be mixed, the plunger being depressable to cause the partition to be severed along its connecting web from the inner surface of the second housing section and thereby to cause the material in the second chamber to drop into and mix with that in the first chamber.

9 Claims, 4 Drawing Figures

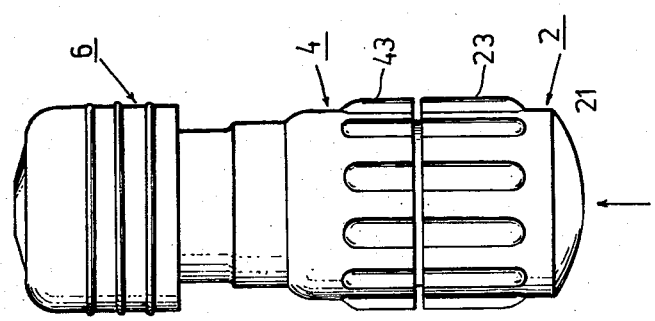
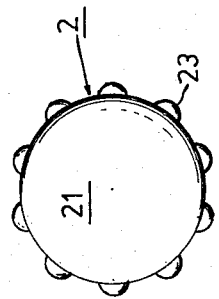
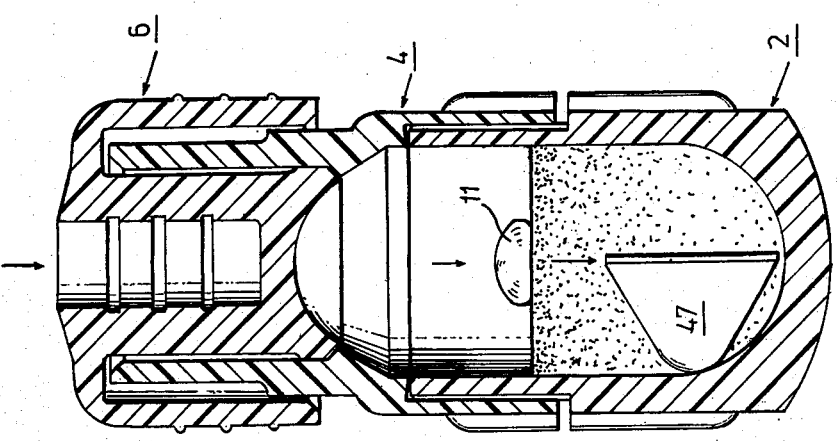
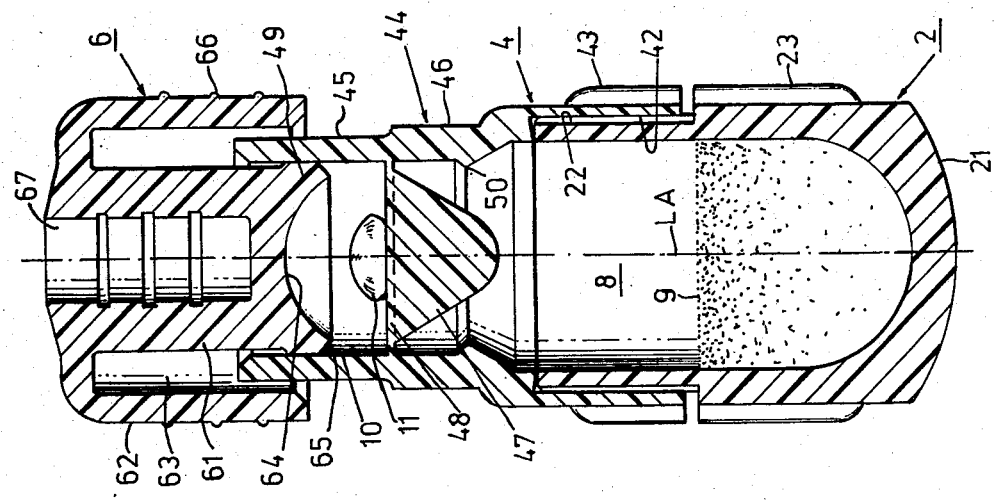

MIXING CAPSULE

BACKGROUND OF THE INVENTION

The present invention relates to mixing capsules, particularly to such capsules in which materials to be mixed are normally kept separated and are brought together only at the time they are to be mixed. One application of such mixing capsules is in the preparation of dental silver amalgams, and the invention is therefore described below particularly with respect to such an application.

In preparing dental silver amalgam for use in filling teeth cavities, a silver alloy is mixed with liquid mercury in a high speed vibrator-mixer. Several different types of mixing capsules have been provided for this purpose. In one of the most popular types, the mercury is kept separated from the silver alloy by means of a plastic partition frictionally retained in a tubular extension of the housing which partition is forced into the mixing chamber by the plunger when depressed by the user. In this type of mixing capsule, however, there is a danger that the partition will drop into the mixing chamber when the capsule is being assembled, or during handling after the materials have been added, the latter causing a premature mixing of the materials. In addition, there is a danger that the mercury may seep around the edges of the partition and enter the mixing chamber prematurely, or that it may seep around the edges of the plunger out of the capsule, particularly during the high-speed mixing after the partition has been removed, the latter especially producing a serious health hazard in view of the highly toxic nature of mercury.

The present invention provides a mixing capsule having advantages in the above respects.

SUMMARY OF THE INVENTION

According to the present invention, there is provided a mixing capsule for mixing a first material with a second material, comprising: a first tubular housing section and a second tubular housing section removably attached to each other and defining between them a first chamber for receiving the first material to be mixed; said first housing section being closed at the bottom and defining the bottom wall of the first chamber; said second housing section including a partition integrally joined to its inner surface by a thin connecting web and serving as a temporary top wall closing the first chamber. The second housing section further includes a tubular neck extending above said partition; and a plunger having a tubular stem disposed in the neck of said second housing section, the lower face of the plunger defining with said partition a second chamber for receiving the second material to be mixed. The plunger is depressable within the neck of the second housing section to cause the partition to be severed along its connecting web from the inner surface of the second section and thereby to cause the material in the second chamber to drop into and mix with that in the first chamber.

In the preferred embodiment of the invention described below, the lower face of the plunger is formed with a recess of sufficient depth that depression of the plunger is engageable with the partition and severs the connecting web before the plunger applies a compressive force to the material in the second chamber.

Preferably, the lower face of the plunger is of concave configuration and is circumscribed by a relatively sharp annular edge.

Also in the described preferred embodiment, the partition is of sufficient mass such that when it is severed from its connecting web and dropped into the first chamber, it facilitates the mixing of the two materials therein.

Further features and advantages of the invention will be apparent from the description below.

BRIEF DESCRIPTION OF THE DRAWINGS

The invention is herein described, by way of example only, with reference to the accompanying drawings, wherein:

FIG. 1 is a side elevational view of one form of mixing capsule constructed in accordance with the invention;

FIG. 2 is a bottom view of the capsule of FIG. 1;

FIG. 3 is an enlarged longitudinal sectional view of the capsule of FIG. 1; and

FIG. 4 is a view corresponding to that of FIG. 3 but showing the capsule after the partition has been severed and has dropped into the mixing chamber to enable the mixing of the two materials contained in the capsule.

DESCRIPTION OF THE PREFERRED EMBODIMENT

The mixing capsule illustrated in the drawings comprises three main components, namely: a bottom housing section 2; a top housing section 4; and a depressable plunger 6. The bottom and top housing sections 2 and 4 are removably attached to each other to define between them a first chamber 8 adapted to contain one of the materials 9 (e.g., silver alloy) to be mixed; and the plunger 6 is slidably received within the upper housing section 4 to define with it an upper chamber 10 adapted to contain the other material 11 (e.g. mercury) to be mixed.

More particularly, the lower housing section 2 is of tubular shape and is formed with a closed bottom wall 21 defining the bottom of chamber 8. The upper end of section 2 is open but is undercut along its outer surface, as shown at 22 for slidably receiving the lower end of the upper housing section 4. In addition, the outer face of the lower housing section 2 is formed with a plurality of axially-extending, circumferentially spaced ribs 23.

The upper housing section 4 is similarly of tubular shape, and its lower end is undercut along its inner surface, as shown at 42, to slidably receive the open end of the lower housing section 2. The upper housing section 4 is also formed with a plurality of axially-extending, circumferentially-spaced ribs 43 adapted to be aligned with ribs 23 of section 2 when the two sections are assembled together. Ribs 23 and 43 facilitate the application of the mixing capsule to the vibrator-mixer, and are commonly provided in such mixing capsules.

The upper end of housing section 4 is formed with a tubular neck 44 having a uniform internal diameter for substantially its complete length, but having an outer diameter which is slightly smaller at its upper portion 45 than at its lower portion 46. A partition 47 is integrally joined to the inner surface of neck 44 by means of a thin connecting web 48 approximately at the juncture between portions 45 and 46. Partition 47 serves as a temporary top wall for chamber 8 and a bottom wall for chamber 10 but may be severed along its thin connecting web 48, in the manner to be described more particularly below, to drop into chamber 8 and thereby to permit the materials 9 and 11 to come together in chamber 8.

The upper housing section 4, as well as the two other components 2 and 6 of the mixing capsule, are preferably made by injection moulding of plastics material. Accordingly, it is a relatively simple matter to form the temporary partition 47 integrally with the upper housing section 4 during the injection moulding of the latter section.

The temporary partition 47 is of sufficient mass such that, after it has been severed along its connecting web 48 and has dropped into chamber 8, it serves as a pestle or agitator during the mixing operation to enhance the mixing of the two materials within chamber 8. An annular rib 50 is formed along the inner surface of neck 44 at its lower end below partition 47.

Plunger 6 includes a stem 61 having an outer diameter substantially equal to the inner diameter of neck 44 of housing section 4, and with an annular skirt 62 coaxial with stem 61 but spaced from the stem a distance equal to the thickness of portion 46 of neck 44. The latter portion 46 of neck 44 is slidably received within the annular space 63 between stem 61 and skirt 62, and engages the confronting faces of the stem and sleeve to provide an effective seal between the plunger and neck 44 of the upper housing section 4 during the mixing operation.

The lower face 64 of stem 61 is formed with a recess, being of an inwardly dished or concave configuration, and is circumscribed by a relatively sharp annular edge 65 at its lowermost portion, which annular edge is spaced slightly inwardly from the outer periphery of the plunger. The depth of the concave face 64 of the plunger stem 61 is such that the volume of chamber 10 will always be larger than the volume of the material 11 within that chamber until the connecting web 48 is severed. This assures that when the plunger is depressed, it will not apply a compressive pressure to the material 11 (e.g. mercury) within chamber 10 before the partition element 46 is severed, since this might cause the mercury to seep out of the capsule even though a relatively good seal is effected between neck 44 and the plunger stem 61 and skirt 62 as described above.

The outer surface of plunger skirt 62 is preferably formed with a plurality of annular ribs 66, to facilitate the application of the capsule to the vibrator-mixer. In addition, plunger stem 61 is preferably of a hollow configuration, as shown at 67, to save material and to reduce shrinking during the injection-moulding of the plunger.

The mixing capsule illustrated in the drawings is used in the following manner.

First, the capsule is loaded with the two materials to be eventually mixed, by introducing one material 9 (e.g. silver alloy) within chamber 8 while the lower housing section 2 is detached from the upper housing section 4; slipping the upper housing section 4 onto the lower housing section 2; introducing the second material 11 (e.g. mercury) into the upper portion 45 of neck 44 of the upper housing section 4; and then applying the plunger 6 over the upper end of the neck by inserting the latter into the annular space 63 between stem 61 and skirt 62 of the plunger 6. The parts would thereby be in the position illustrated in FIG. 2 of the drawings, with the material 9 in chamber 8 separated from the material 11 in chamber 10 by the partition element 47 which is integrally joined to neck 44 of the upper housing section 4 by the thin connecting web 48. In such a condition, the material 11 in chamber 10 is protected from leaking into chamber 8 by the partition element 47 and its connecting web 48, and is protected against leaking externally of the capsule by the seal effected between the inner surface of neck 44 and the outer surface of the plunger stem 61 with which it contacts.

When the materials within compartments 8 and 10 are to be mixed, plunger 6 is depressed until its stem 61 limits against annular rib 50. Depression of the plunger causes its annular edge 65 at the lower face of its stem 61 to effect the severance of web 48, such that when stem 61 finally limits against annular rib 50, the connecting web 48 will have been completely severed, and the partition element 47, together with the material 11 in chamber 10, will have been positively forced into chamber 8. In this fully depressed position of the plunger, the inner surface of its skirt engages the outer surface of neck portion 46, thereby enhancing the seal between the neck and the plunger.

The capsule is then applied to a vibrator-mixer in the normal manner, whereupon the two materials now in chamber 8 become intimately mixed, the mixing being enhanced by the pestle action of element 47 within chamber 8.

If desired, the outer annular edge 65 of the plunger could be serrated to facilitate its cutting of the thin connecting web 48.

While the invention has been described with respect to one preferred embodiment, it will be appreciated that many variations, modifications and other applications of the invention may be made.

What is claimed is:

1. A mixing capsule for mixing a first material with a second material, comprising: a first tubular housing section and a second tubular housing section removably attached to each other and defining between them a first chamber for receiving the first material to be mixed; said first housing section being closed at the bottom and defining the bottom wall of the first chamber; said second housing section including a partition integrally joined to its inner surface by a thin connecting web and serving as a temporary top wall closing the first chamber; said second housing section further including a tubular neck extending above said partition; and a plunger having a tubular stem disposed in the neck of said second housing section; the lower face of the plunger defining with said partition a second chamber for receiving the second material to be mixed; said plunger being depressable within the neck of the second housing section to cause the partition to be severed along its connecting web from the inner surface of the second housing section and thereby to cause the material in the second chamber to drop into and mix with that in the first chamber; the lower face of said plunger being engageable with said partition and being formed with a recess of sufficient depth that depression of the plunger severs the connecting web before the plunger can apply a compressive force to the material in the second chamber.

2. A mixing capsule according to claim 1, wherein the lower face of the plunger is of concave configuration and is circumscribed by a relatively sharp annular edge.

3. A mixing capsule according to claim 1, wherein the second housing section is formed with an annular rib on its inner surface below the partition and serving as a limit for the depression of the plunger, said annular rib being sufficiently below the partition to assure a complete severance of the connecting web before the annular rib limits the further depression of the plunger.

4. A mixing capsule according to claim 1, wherein said partition is of sufficient mass such that when it is severed from its connecting web and drops into the first chamber, it facilitates the mixing of the two materials therein.

5. A mixing capsule according to claim 1, wherein said plunger includes a stem and an outer skirt coaxial with and spaced from the stem by the thickness of said neck of the second housing section, the outer surface of the stem and the inner surface of the skirt contacting the inner and outer surfaces of said neck and being slidable therealong during the depression of the plunger to form an effective seal with said neck.

6. A mixing capsule according to claim 1, wherein the two tubular housing sections are formed with undercuts for slidably connecting them together.

7. A mixing capsule according to claim 1, wherein said plunger is slidable within the neck of the second housing section.

8. A mixing capsule for mixing a first material with a second material, comprising: a first tubular housing section and a second tubular housing section removably attached to each other and defining between them a first chamber for receiving the first material to be mixed; said first housing section being closed at the bottom and defining the bottom wall of the first chamber; said second housing section including a partition integrally joined to its inner surface by a thin connecting web and serving as a temporary top wall closing the first chamber; said second housing section further including a tubular neck extending above said partition and a plunger having a tubular stem disposed in the neck of said second housing section; the lower face of the plunger defining with said partition a second chamber for receiving the second material to be mixed; said plunger being depressable within the neck of the second housing section to cause the partition to be severed along its connecting web from the inner surface of the second housing section and thereby to cause the material in the second chamber to drop into and mix with that in the first chamber; said partition being of sufficient mass such that when it is severed from its connecting web and drops into the first chamber, it facilitates the mixing of the two materials therein.

9. A mixing capsule according to claim 8, wherein the lower face of said plunger is engageable with said partition and is formed with a recess of sufficient depth that depression of the plunger severs the connecting web before the plunger can apply a compressive force to the material in the second chamber.

* * * * *